US00PP30485P2

(12) United States Plant Patent
van Leeuwen

(10) Patent No.: US PP30,485 P2
(45) Date of Patent: May 7, 2019

(54) ***PHLOX* PLANT NAMED 'GREEN LION'**

(50) Latin Name: *Phlox paniculata*
Varietal Denomination: Green Lion

(71) Applicant: Van Leeuwen Bloemen BV, Horst (NL)

(72) Inventor: Jan van Leeuwen, Horst (NL)

(73) Assignee: VAN LEEUWEN BLOEMEN BV, Horst (NL)

( * ) Notice: Subject to any disclaimer, the term of this patent is extended or adjusted under 35 U.S.C. 154(b) by 0 days.

(21) Appl. No.: 15/932,412

(22) Filed: Feb. 27, 2018

(51) Int. Cl.
*A01H 5/02* (2018.01)

(52) U.S. Cl.
USPC ..... Plt./320

(58) Field of Classification Search
USPC ..... Plt./263.1, 320
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Phlox*, 'Green Lion' that is characterized by its inflorescences that are dark green in color, its compact plant habit, upright plant habit, its flower buds do not open, its high resistance to powdery mildew, its long lasting ornamental value, and its suitability as a garden plant and as a cut flower.

2 Drawing Sheets

Botanical classification: *Phlox paniculata.*
Cultivar designation: 'Green Lion'.

BACKGROUND OF THE INVENTION

The present invention relates to a new and distinct cultivar of *Phlox* plant, botanically known as *Phlox paniculata* 'Green Lion' and will be referred to hereafter by its cultivar name, 'Green Lion'. The new cultivar represents a new herbaceous perennial grown for landscape use.

The Inventor discovered the new cultivar in June of 2016 as a naturally occurring branch mutation of *Phlox paniculata* 'Blind Lion' (U.S. Plant Pat. No. 26,255) in a production field at his nursery in Horst, The Netherlands.

Asexual propagation of the new cultivar was first accomplished by tissue culture using meristem tissue in Delft, The Netherlands in April of 2017 under the direction the Inventor. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Green Lion' as a new and unique cultivar of *Phlox.*

1. 'Green Lion' exhibits inflorescences that are dark green in color.
2. 'Green Lion' exhibits a compact plant shape.
3. 'Green Lion' exhibits flower buds do not open.
4. 'Green Lion' exhibits high resistance to powdery mildew.
5. 'Green Lion' exhibits long lasting ornamental value.
6. 'Green Lion' exhibits characteristics suitable as a garden plant and as a cut flower.

The parent plant of 'Green Lion', 'Blind Lion', differs from 'Green Lion' in having inflorescences that are dark purple-brown in color and in being taller in height. 'Green Lion' can be compared to the *Phlox* cultivars 'Green Princess' (not patented) and 'Empty Feelings' (U.S. Plant Pat. No. 12,969). Both are similar to 'Green Lion' in having inflorescences that are similar in shape. 'Green Princess' differs from 'Green Lion' in having a less compact plant habit and inflorescences that are lighter green in color. 'Empty Feelings' differs from 'Green Lion' in having a less compact plant habit and inflorescences that are less green in color.

BRIEF DESCRIPTION OF THE DRAWINGS

The accompanying colored photographs illustrate the overall appearance and distinct characteristics of the new *Phlox*. The photographs were taken of a one year-old plant of 'Green Lion' as grown outdoors in a 2-liter container in Horst, The Netherlands and placed in a 2-liter container for the photographs.

The photograph in FIG.1 provides a side-view of a plant of 'Green Lion' in bloom.

Figure 1:
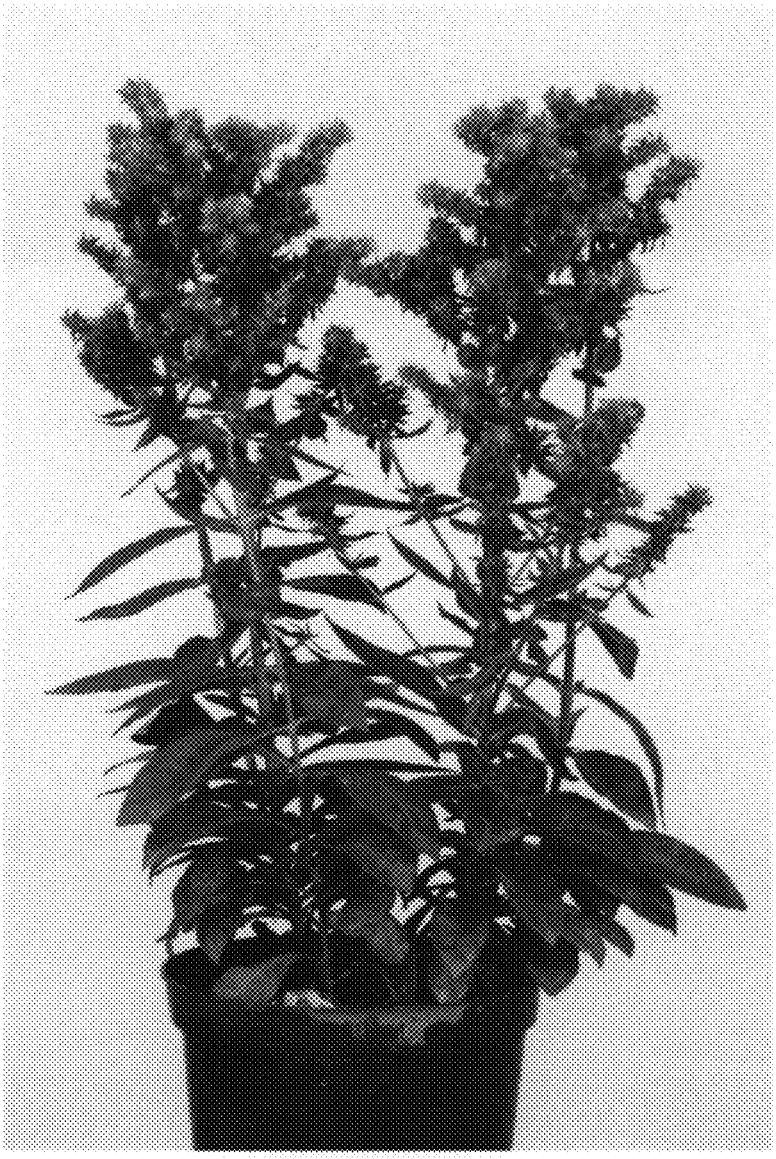
Figure 2:
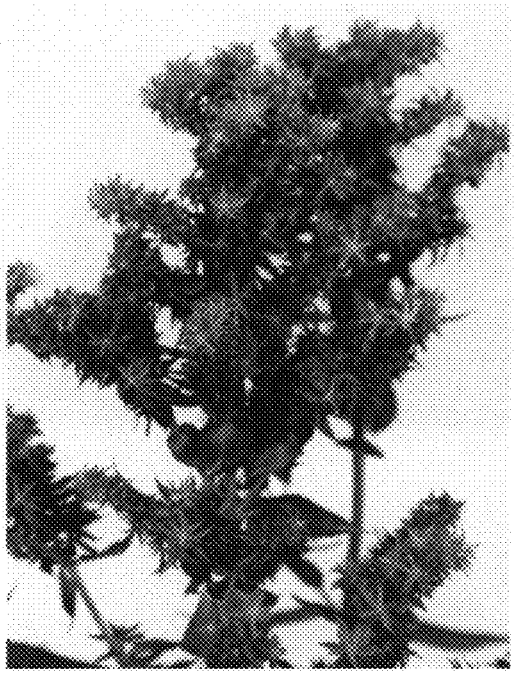

The photograph in FIG. 2 provides a close-up view of an inflorescence of 'Green Lion' showing the unopened flowers.

Figure 3:
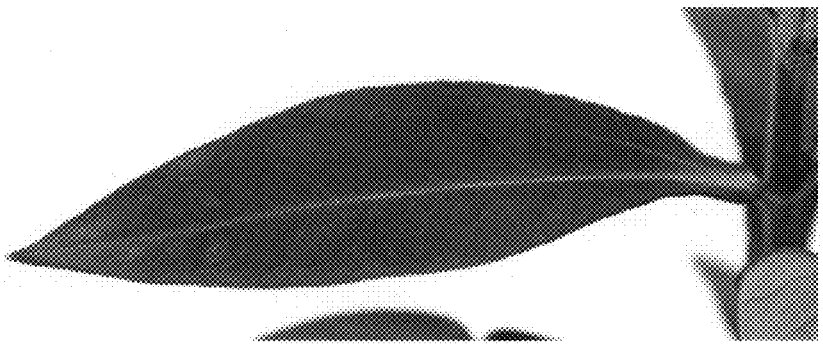

The photograph in FIG. 3 provides a close-up view of a leaf of 'Green Lion'.

The colors in the photographs may differ slightly from the color values cited in the detailed botanical description, which accurately describe the colors of the new *Phlox.*

DETAILED BOTANICAL DESCRIPTION OF THE PLANT

The following is a detailed description of one year-old plants of the new cultivar as grown outdoors in 2-liter containers in Horst, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Early June to mid-September in The Netherlands.

*Plant type.*—Herbaceous perennial.

*Plant habit.*—Compact, upright.

*Height and spread.*—An average of 29.8 cm in height (soil level to top of foliar plane), an average of 39.6 cm in height (soil level to top of floral plane), 31.2 cm in diameter as grown in a 2-liter container.

*Cold hardiness.*—At least in U.S.D.A. Zone 4.

*Diseases.*—Highly resistant to powdery mildew caused by *Erysiphe cichoracearum.*

*Root description.*—Fine and fibrous.

*Growth rate.*—Moderate.

*Root development.*—An average of 6 weeks for root initiation, 10 weeks to produce a fully rooted cutting, 3 to 4 months from a rooted cutting to produce a young finished plant.

*Propagation.*—Tissue culture.

Stem description:

*Stem size.*—Average of 26.2 cm in length (excluding inflorescence), 4 mm in diameter.

*Stem shape.*—Rounded.

*Stem strength.*—Strong.

*Stem color.*—Young stems 144A, mature stems 144B.

*Stem surface.*—Glabrous, moderately glossy.

*Stem aspect.*—Main stems held at an average angle of 20° to vertical, lateral stems held at an average angle of 40° to main stems.

*Internode length.*—An average of 3.3 cm.

*Branching habit.*—Stems emerge from base, an average of 5 main stems per plant, 8 lateral branches per main branch.

Foliage description:

*Leaf shape.*—Elliptic and slightly carinate.

*Leaf division.*—Simple.

*Leaf base.*—Truncate.

*Leaf apex.*—Acute to slightly acuminate.

*Leaf venation.*—Pinnate, upper surface 144A, lower surface 144B.

*Leaf margins.*—Entire.

*Leaf attachment.*—Petiolate.

*Leaf arrangement.*—Opposite.

*Leaf surface.*—Both surfaces slightly glossy and glabrous.

*Leaf color.*—Young upper surface; 137C, young lower surface; between 137C and 146B, mature upper surface; NN137A, mature lower surface; 147B.

*Leaf size.*—An average of 8.8 cm in length and 3 cm in width.

*Leaf quantity.*—An average of 26 per stem.

*Leaf fragrance.*—None.

*Petioles.*—V-shaped, an average of 3 mm in width and 2 mm in length, upper surface; 144C, lower surface; 145A, surfaces are glabrous.

Flower description:

*Inflorescence type.*—Compound terminal panicle of flower buds surrounded by showy bracts.

*Lastingness of inflorescence.*—6 to 8 weeks.

*Lastingness as a cut flower.*—12 to 16 weeks.

*Inflorescence size.*—An average of 16.3 cm in height and 11.8 cm in diameter.

*Flower fragrance.*—None.

*Flower number.*—An average of 1,000 per inflorescence, 5,0000 per plant.

*Flower aspect.*—Upright to outward.

*Flower bud.*—An average of 2 mm in length and 1 mm in width, slightly glossy, ovate in shape, 144B in color.

*Flower form.*—Numerous bracts with no reproductive organs, flowers remain in the bud stage and do not open.

*Bracts.*—An average of 1, narrow elliptic in shape, an average of 7 mm in length, and 2.5 mm in width, narrowly acuminate apex, cuneate base, both surfaces young color 144B, upper surface mature color 137A, lower surface mature color 137B.

*Sepals.*—Not described as the flowers do not open.

*Petals.*—Not described as the flowers do not open.

*Peduncles.*—An average of 14.7 cm in length, 2.5 mm in diameter, strong, smooth and glabrous, moderately glossy, 144A in color, terminal peduncle is held straight upright, secondary peduncle is held in an average angle of 45°.

*Reproductive organs.*—No reproductive organs were formed; the flowers do not open.

*Seed/fruit.*—None are produced.

It is claimed:

1. A new and distinct cultivar of *Phlox* plant named 'Green Lion' as herein illustrated and described.

* * * * *